(12) United States Patent  (10) Patent No.: US 7,960,441 B2
Wolf  (45) Date of Patent: Jun. 14, 2011

(54) METHOD FOR REPROCESSING COMBUSTION PRODUCTS FROM FOSSIL FUELS

(75) Inventor: Bodo Max Wolf, Mindelheim (DE)

(73) Assignee: BW-Energiesysteme GmbH, Dresden (DE)

( * ) Notice: Subject to any disclaimer, the term of this patent is extended or adjusted under 35 U.S.C. 154(b) by 119 days.

(21) Appl. No.: 12/375,825

(22) PCT Filed: Jun. 28, 2007

(86) PCT No.: PCT/EP2007/005706
§ 371 (c)(1),
(2), (4) Date: Mar. 31, 2009

(87) PCT Pub. No.: WO2008/014854
PCT Pub. Date: Feb. 7, 2008

(65) Prior Publication Data
US 2009/0307975 A1  Dec. 17, 2009

(30) Foreign Application Priority Data
Jul. 31, 2006 (DE) .......................... 10 2006 035 893

(51) Int. Cl.
*C07C 27/00* (2006.01)
(52) U.S. Cl. .......................... 518/700; 518/702; 518/704
(58) Field of Classification Search .................. 518/700, 518/702, 704
See application file for complete search history.

(56) References Cited

U.S. PATENT DOCUMENTS

| 5,312,843 A | 5/1994 | Yamauchi et al. |
| 5,416,245 A | 5/1995 | MacGregor et al. |
| 2004/0245086 A1* | 12/2004 | Steynberg et al. ............ 204/164 |
| 2006/0211777 A1* | 9/2006 | Severinsky .................. 518/702 |

FOREIGN PATENT DOCUMENTS

| WO | WO 01/38456 A1 | 5/2001 |
| WO | WO 03/018467 A2 | 3/2003 |
| WO | WO 03/029174 A2 | 4/2003 |
| WO | WO 2005/005009 A2 | 1/2005 |
| WO | WO 2006/099573 A1 | 9/2006 |
| WO | WO 2007/108014 A1 | 9/2007 |

* cited by examiner

*Primary Examiner* — Jafar Parsa
(74) *Attorney, Agent, or Firm* — Foley & Lardner LLP

(57) ABSTRACT

The present invention relates to a method for reprocessing of the combustion products, carbon dioxide and water, to generate renewable synthetic fuels and motor fuels by means of electrical energy, involving, according to the invention, mixing hydrogen, produced from water, preferably water vapor, by electrolysis, and carbon dioxide up to a molar ratio of 1 to 3.5 to obtain a carbon dioxide-hydrogen mixture, pre-heating said mixture in a high temperature recuperator and then heating it to 800 to 5,000° C. in an electrically-heated device or an electrical plasma generator, utilizing the crude synthesis gas thus formed recuperatively to pre-heat the carbon dioxide-hydrogen mixture, then directly cooling while the reaction water separates, and feeding the carbon monoxide-carbon dioxide-hydrogen mixture existing at this stage to a Fischer-Tropsch or methanol synthesis and converting it therein to the products, hydrocarbons and/or methanol, which are cooled while the water separates, and are condensed if necessary.

9 Claims, 1 Drawing Sheet

METHOD FOR REPROCESSING COMBUSTION PRODUCTS FROM FOSSIL FUELS

CROSS-REFERENCE TO RELATED APPLICATION

This application is a National Stage Entry of PCT/EP07/05706.

The invention is related to a method for reprocessing or recycling, respectively, of the combustion products, carbon dioxide and water, such as are present in the exhaust gases of combustion processes or in the environment, to generate renewable synthetic fuels and motor fuels by means of electrical energy that was not produced by means of fossil fuels.

The application field of the invention is the global, regional, and local supply of regenerative energy in the form of substance-bound chemical energy to industry, commerce, municipalities, and buildings.

Until recently, the prior art considered the combustion of fossil fuels to be an irreversible process, i.e. combustion is a process that proceeds in the direction of the combustion products only. In practical application, this was applied to conclude that it is impossible or not reasonable to re-produce from the combustion products fuels of the type of fossil fuels, i.e. hydrocarbons. This scientific opinion was formed as a result of thermodynamics being based on the balance cycle on Earth. This teaching has been disproved by the publication, "Öl aus Sonne, die Brennstoffformel der Erde", Ponte Press Verlag GmbH, ISBN 3-920328-49-3. The publication describes that the combustion process of fossil fuels, which proceeds in an exothermic fashion when oxygen is added, is part of natural reversible conversion of substances that can be reversed by re-introducing energy.

It is therefore the technical object of the invention to propose a technical solution that can be used to reverse the process of combustion.

The technical object is achieved according to the invention by separating the oxygen, which gets bound to carbon and hydrogen in the process of combustion, from the combustion products, carbon dioxide and water, by introducing electrical energy that was produced mainly by means of regenerative energy carriers, but not by means of fossil fuels, by mixing hydrogen, produced from water or preferably water vapor (respectively steam) by electrolysis, and carbon dioxide up to a molar ratio of 1 to 3.5 to obtain a carbon dioxide-hydrogen mixture, pre-heating said mixture in a high temperature recuperator and then heating it to 800 to 5,000° C. in an electrically-heated device or an electrical plasma generator, utilizing the crude synthesis gas thus formed recuperatively to pre-heat the carbon dioxide-hydrogen mixture, then directly cooling while the reaction water separates and feeding the obtained carbon monoxide-carbon dioxide-hydrogen mixture existing at this stage to a Fischer-Tropsch or methanol synthesis and converting it therein to the products, hydrocarbons and/or methanol, which are cooled while the water separates and are condensed if necessary.

The invention also includes that the recuperative pre-heating and the further heating of the carbon dioxide-hydrogen mixture involve the supply of electrical energy in the presence of catalysts.

Furthermore, the invention also includes using the water obtained during the gas and product cooling jointly with external water for direct cooling of the crude synthesis gas and synthesis processes, evaporating it in the process, and cleaving the vapor into hydrogen and oxygen in the electrolysis.

The economic advantage of the invention is based on the conversion of regenerative energy into renewable fuels that can fully substitute for fossil fuels and can be distributed via the existing infrastructure and which, since they can be stored at ambient pressure and temperature and since the sources of regenerative energy are inexhaustible by man, can be used to assure that the supply of energy carriers and chemical substances meets the demand at all times independent of the fossil fuels. Unlike the hydrogen system that is being proposed, the application of the invention is associated, in particular, with an economic advantage in that existing energy systems, which represent several trillion Euros of fixed capital, can continue to be operated and investments of the same order of magnitude for setting-up a new hydrogen-suited infrastructure can be avoided. The invention provides the foundations for the smooth transition from a fossil to a solar substance and energy economy.

BRIEF DESCRIPTION OF THE DRAWINGS

The invention is illustrated more closely in an exemplary embodiment together with the appended FIGURE.

DETAILED DESCRIPTION OF THE PREFERRED EMBODIMENTS

Exemplary Embodiment

Figure 1:
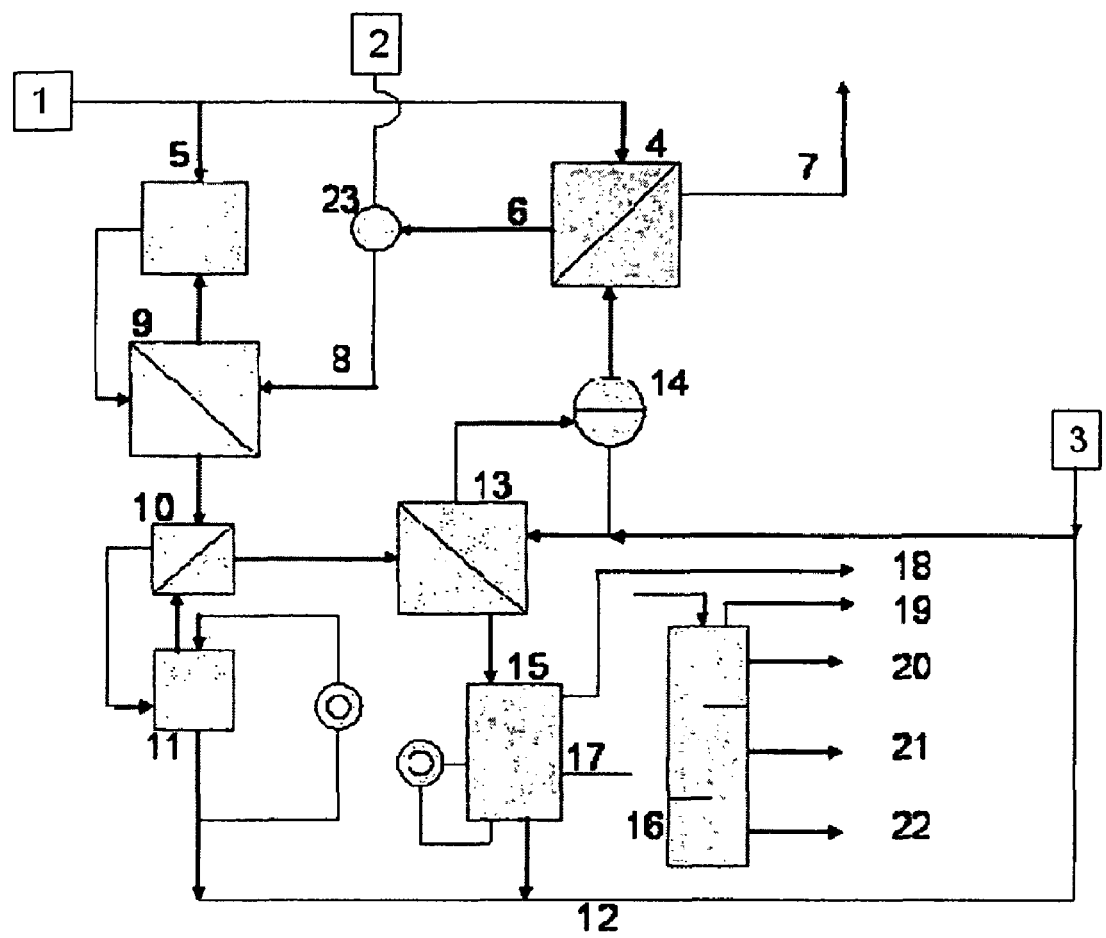

According to the invention, carbon dioxide and water are converted to alcohol or hydrocarbons such as methane, gasoline, Diesel, and wax by means of regenerative energy that was converted to electrical energy. For this purpose, electrical energy, carbon dioxide, and water are supplied to the process via 1, 2, and 3, respectively. In cooling 14 of synthesis reactor 13, the water is evaporated jointly with water condensate that is obtained in the direct gas cooling 11 and product cooling 15 and collected via condensate collector 12, preferably at a pressure of 20 bar, and the water vapor is cleaved in the electrolysis 4 into hydrogen 6 and oxygen 7.

The hydrogen 6 is mixed in 23 with the carbon dioxide supplied via 2 at a molar ratio of preferably 3:1 at a pressure of 19 bar and the carbon dioxide-hydrogen mixture 8 is pre-heated, optionally in the presence of a catalyst, to 600 to 800° C. in the high temperature recuperator 9 in a counter-current arrangement with respect to the crude synthesis gas that is supplied from the electrically-heated device 5 and has a temperature in excess of 900° C. The pre-heated gas mixture 8 is fed into the electrically-heated device 5 and heated therein to at least 900° C. in the presence of a catalyst. The supply of energy in the electrically-heated device 5 converts the carbon dioxide-hydrogen mixture 8 to a crude synthesis gas with a joint carbon monoxide and hydrogen fraction of approximately 65 volume-%. The rest is water vapor and uncleaved carbon dioxide. The crude synthesis gas is cooled in the recuperator 10 and by direct cooling with cold water in 11 to less than 50° C., which is associated with condensation and separation of reaction water, and then re-heated in the recuperator 10 before it is fed to the synthesis reactor 13, now as synthesis gas. Depending on the production goal and correspondingly added catalyst, the synthesis gas is converted to methane-containing gas 18 and/or methanol or liquid hydrocarbons (gasoline, kerosine, Diesel) or wax in the synthesis reactor 13. In case methanol and liquid hydrocarbons are produced, condensation of the products and separation of product water are effected by cooling in the product collection container 15. In case liquid hydrocarbons are produced, the substances are separated at a small over-pressure into gasoline 20, Diesel 21, and wax 22 in the distillation 16, while flash gas 19 separates. The water-depleted product is fed from the product collection container 15 to the distillation 16 and the pressure is reduced via 17.

The invention claimed is:

1. Method for reprocessing the combustion products, carbon dioxide and water, to generate renewable synthetic fuels and motor fuels by means of electrical energy, characterized by mixing hydrogen, produced from water, by electrolysis, and carbon dioxide up to a molar ratio of 1 to 3.5 to obtain a carbon dioxide-hydrogen mixture, pre-heating said mixture in a high temperature recuperator to 600 to 800° C. and then heating it to a temperature ranging from above 800 to 5,000° C. in an electrically-heated device or an electrical plasma generator, thereby forming a crude synthesis gas, containing carbon monoxide, hydrogen, reaction water vapour and uncleaved carbon dioxide, utilizing the crude synthesis gas recuperatively in the high temperature recuperator to pre-heat the carbon dioxide-hydrogen mixture, pre-cooling the crude synthesis gas in a second recuperator, then directly cooling the pre-cooled crude synthesis gas, while the reaction water condenses and is separated from the crude synthesis gas and reheating the water depleted crude synthesis gas, containing carbon monoxide, carbon dioxide and hydrogen, in the second recuperator, and feeding the reheated carbon monoxide-carbon dioxide-hydrogen mixture to a Fischer-Tropsch or methanol synthesis and converting it therein to the products, hydrocarbons and/or methanol, which are cooled while the thereby produced water condenses and separates, whereby the products and are condensed if necessary.

2. Method according to claim 1, wherein the recuperative pre-heating and the further heating of the carbon dioxide-hydrogen mixture involve the supply of electrical energy in the presence of catalysts.

3. Method according to claim 1, wherein the water obtained during the crude synthesis gas and product cooling is used jointly with external water for cooling of the crude synthesis gas and for cooling of the Fischer-Tropsch or methanol synthesis processes, in order to evaporate it in the process and to feed the obtained water vapor in elektrolyzer for cleaving the vapor into hydrogen and oxygen in the electrolysis.

4. Method according to claim 2, wherein the water obtained during the crude synthesis gas and product cooling is used jointly with external water for cooling of the crude synthesis gas and for cooling of the Fischer-Tropsch or methanol synthesis processes, in order to evaporate it in the process and to feed the obtained water vapor in elektrolyzer for cleaving the vapor into hydrogen and oxygen in the electrolysis.

5. Method according to claim 1, wherein the crude synthesis gas and the carbon dioxide-hydrogen mixture are conducted counter currently in the high temperature recuperator.

6. Method according to claim 2, wherein the crude synthesis gas and the carbon dioxide-hydrogen mixture are conducted counter currently in the high temperature recuperator.

7. Method according to claim 1, wherein the crude synthesis gas from the high temperature recuperator and the direct cooled water depleted crude synthesis gas are conducted counter currently in the second recuperator.

8. Method according to claim 2, wherein the crude synthesis gas from the high temperature recuperator and the direct cooled water depleted crude synthesis gas are conducted counter currently in the second recuperator.

9. Method according to claim 1, wherein the hydrogen is produced from water vapor by electrolysis.

* * * * *